United States Patent [19]

Williams

[11] Patent Number: 5,171,523

[45] Date of Patent: * Dec. 15, 1992

[54] METHOD AND APPARATUS FOR DISINFECTING OBJECTS

[76] Inventor: Robert M. Williams, 705 Kenyon St., NW., Washington, D.C. 20010

[*] Notice: The portion of the term of this patent subsequent to Aug. 20, 2008 has been disclaimed.

[21] Appl. No.: 434,851

[22] Filed: Nov. 1, 1989

Related U.S. Application Data

[63] Continuation-in-part of Ser. No. 252,522, Oct. 3, 1988, Pat. No. 5,041,264.

[51] Int. Cl.$^5$ ............................................. A61L 2/16
[52] U.S. Cl. ............................. 422/20; 422/28; 422/294; 206/205; 206/210; 383/40
[58] Field of Search .............. 422/20, 25, 28, 33, 422/36, 37, 294, 300; 206/205, 210, 610, 67.1; 383/4, 33, 34, 40, 75, 76, 72

[56] References Cited

U.S. PATENT DOCUMENTS

| | | | |
|---|---|---|---|
| 1,817,530 | 8/1931 | Spanel | 422/294 |
| 1,817,532 | 8/1931 | Spanel | 422/294 |
| 1,817,534 | 8/1931 | Spanel | 422/294 |
| 2,572,669 | 10/1951 | Sarge et al. | 422/294 |
| 4,349,104 | 9/1982 | Hayes | 206/205 |
| 4,362,241 | 12/1982 | Williams | 206/210 |
| 4,517,159 | 5/1985 | Karlson | 422/20 |
| 5,041,264 | 8/1991 | Williams | 422/28 |

FOREIGN PATENT DOCUMENTS 0236071 10/1960 Australia ............................ 422/294

*Primary Examiner*—Robert J. Warden
*Assistant Examiner*—William H. Beisner
*Attorney, Agent, or Firm*—Beveridge, DeGrandi & Weilacher

[57] ABSTRACT

Contaminated objects are disinfected in a device which has a cavity formed by a fluid impermeable wall, an opening that is closeable by a seal, and a dispensing conduit which is spaced from the seal. Objects are placed in the cavity, the opening is sealed, and a disinfectant soluiton is introduced into the dispensing conduit. The disinfectant solution flows from outlets in the conduit into the cavity so that the objects in the cavity are disinfected by the solution and its vapors.

22 Claims, 3 Drawing Sheets 5,171,523

METHOD AND APPARATUS FOR DISINFECTING OBJECTS

REFERENCE TO RELATED APPLICATION

This is a continuation-in-part of U.S. Pat. application No. 07/252,522, filed Oct. 3, 1988, the entire contents of which are incorporated herein by reference.

BACKGROUND OF THE INVENTION

This invention is directed to a disinfection apparatus and method which is particularly suited for use in the healthcare field.

Current medical practice involves the use of a large number of disposable objects including syringes, garments, surgical drapes, dressings, hemostats, cotton tip applicators, speculums and other such items. In the course of normal use, these objects often come into contact with individuals who have infectious diseases, thus raising a possibility that infected objects may later transmit infections or diseases to new victims.

There is a significant need for a device and method which will reduce the risk of spreading infection by contact with contaminated disposable waste materials. The present invention provides a device and method which is relatively uncomplicated and quite effective for this purpose, and it is suitable for use in many locations including hospitals, physician's offices, dental offices, or homes.

SUMMARY OF THE INVENTION

The invention involves a device with a cavity for holding objects to be disinfected. The cavity is formed by a wall of sheet material which is substantially impervious to liquids and gases. The device has an opening which permits objects to be inserted into the cavity. Means are provided for introducing a disinfectant solution into a dispensing conduit, and the conduit has outlets which release the disinfectant solution into the cavity. A sealing means is spaced from the dispensing conduit. The sealing means closes the opening, thus retaining the disinfectant solution in the cavity so that the objects placed therein will be disinfected by the solution and its vapors. An absorbent liner of sheet material may be located inside the impervious wall where it will face toward objects placed in the cavity.

Preferably, the wall of the device is formed on laminated sheets of polyester and polyethylene, and the absorbent liner is a sheet of nonwoven fibrous material. Suitable disinfecting solutions include an aqueous solution of calcium hypochlorite, glutaraldehyde, an aqueous solution of sodium hypochlorite, an aqueous solution of isopropyl alcohol, an aqueous solution of ethanol alcohol, or a phenyl solution which may include glutaraldehyde.

The invention also involves a method of disposing of biological materials, contaminated items and other objects. This method is performed by placing such objects in the device described in the two preceding paragraphs, using the sealing means to close and seal the cavity, and introducing the disinfectant solution into the dispensing conduit so that it flows through the outlets into the cavity where the solution and its vapors will disinfect the contaminated objects in the device. The outlets may be positioned above the cavity when the solution is introduced, and the device may be rotated to distribute the solution throughout the cavity.

The invention may be practiced by a wide variety of devices. Exemplary versions are described below and are illustrated in the accompanying drawings.

DETAILED DESCRIPTION

Figure 1:
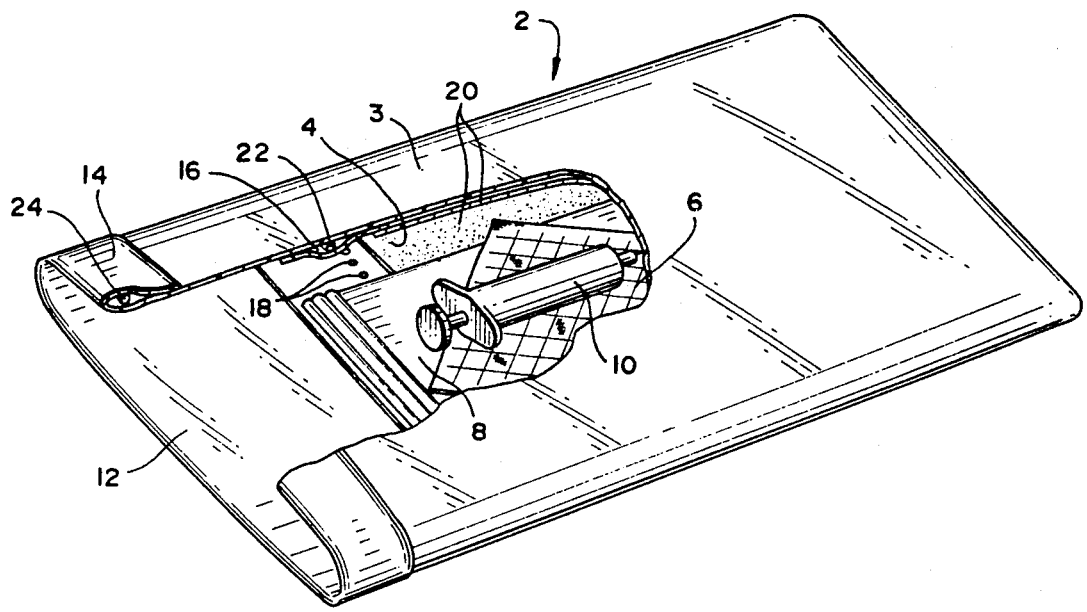
FIG. 1 is a broken perspective view showing the device according to the invention in a flat unsealed condition, with contaminated products having been inserted into the device prior to sealing.

Referring to FIG. 1, it will be seen that the device 2 is a flexible bag formed of a fluid impervious wall 3 of sheet material, the interior of which is a cavity 4 for receiving contaminated objects such as gauze 6, a used surgical drape 8, and a syringe 10. At the end of the device, there is an opening 12 through which contaminated objects are inserted into the cavity 4. Extending circumferentially around the opening 12, there is a hem 14 containing a drawstring 24 which is used to constrict and close the opening as will be described later in this specification.

Spaced downwardly from the opening 12, a dispensing conduit 16 extends around the perimeter of the device. This conduit is formed by fusion bonding the spaced margin portions of an internal circumferential band of plastic material to the internal surface of the wall 3. This provides the space which forms the conduit 16. A plurality of outlet openings 18 are punched in the conduit 16 so that any disinfectant solution in the conduit will flow through the outlets 18 into the cavity of the device.

The interior of the cavity 4 is lined with an absorbent sheet material 20 which preferably is a hydrophilic nonwoven fabric which is well known in the art. The absorbent liner 20 preferably extends circumferentially around the cavity to line the entire wall portion which lies inwardly of the dispensing conduit.

A frangible ampule 22 which contains a disinfectant solution is located in the dispensing conduit 16. When the ampule is broken, the conduit distributes the liquid circumferentially around the cavity 4 so that it can flow through the outlets 18 into the absorbent liner material 20. When thus distributed, the disinfectant solution can contact the contaminated objects and it also vaporizes to provide a disinfecting gas which penetrates the objects to provide a thorough disinfecting action.

To enhance the disinfecting action and to contain any disinfecting solutions and vapors which have a high toxicity, the device is provided with means for sealing the opening 12. The sealing means may be a wire or plastic tie, a mechanical locking arrangement of the type used in plastic bags sold under the trademark ZIP-LOK, or it may be an adhesive coating which, prior to sealing, is covered by a sheet of release paper which prevents premature sealing. In the disclosed embodiment, however, the sealing means includes a drawstring 24 which is spaced a sufficient distance from the contents of the device so that the neck of the bag may be folded at 26 and tied in the manner shown diagrammatically in FIG. 2. The drawstring 24 is wrapped one or more times around the entire device at a point which lies between the fold 26 and the disinfectant conduit 16, pulled taut, and knotted at 28 to assure a hermetic seal.

Figure 3:
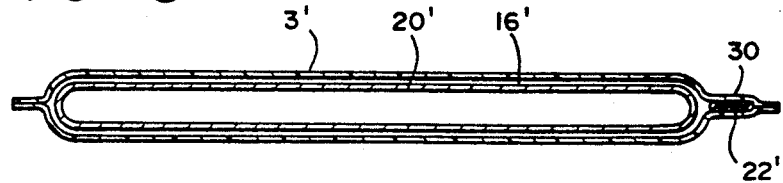
FIG. 3 is a transverse sectional view showing a modified version of the device; version of the device.

In an alternative embodiment of the invention shown in the transverse sectional view of FIG. 3, the dispensing conduit 16' is located on the exterior of the impermeable wall 3' of the bag. Here, the circumferential conduit-forming strip has portions 30 which protrude laterally from the bag to provide a chamber for the frangible ampule 22'. Such an arrangement makes it easier to find the ampule when the user wishes to break it to release the disinfectant solution into the dispensing conduit, absorbent liner 20', and the contents of the device.

Figure 2:
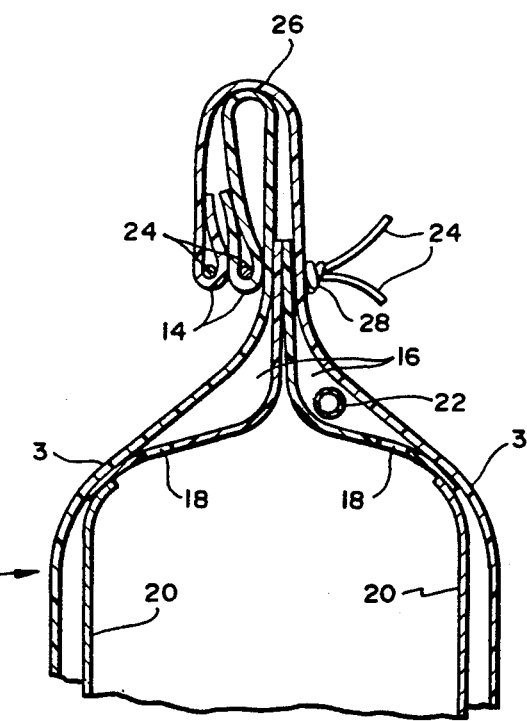
FIG. 2 is a diagrammatic sectional view showing the device in a sealed condition.

The device of the invention can be used as a wastebasket liner, a hanging receptacle, or it may be kept in a drawer, on a shelf or in some other storage location until it is called into use. In any event, contaminated objects such as gauze, syringes or dressings are placed in the device, and the drawstring 24 is pulled to constrict and close the opening 12. To assure that the seal is complete, the constricted neck is folded and gathered as shown in FIG. 2, and the ends of the drawstring 24 are wrapped around the entire neck and tied so that vapors cannot escape from the device. Then, the user breaks the ampule. The released disinfectant solution will then flow circumferentially around the bag in the distribution conduit, and then flow through the outlets 18 into the bag contents and absorbent liner. The disinfectant liquid and its vapors will then disinfect the bag contents so that the entire package can be disposed of without risk of contaminating persons who come into contact with it.

A variety of materials are suitable for forming the wall 3 of the bag, but it is important that such materials be impervious to fluids including liquid and gas. A preferred material of this nature is a bag formed of laminated sheet material having a layer of polyester adhesively bonded to a layer of polyethylene. The polyester has a 48 gage thickness, and the polyethylene has a thickness of 1.5 mil, thus providing a total thickness of approximately 2 to 3 mils. Such a product is available from Jaite Packaging, Inc., Akron, Ohio 44313. Other suitable bags can be formed of polyethylene or polyester with metallized foil layers thereon to obstruct the escape of liquids and vapors from the cavity 4 of the device.

The disinfectant solution is preferably a 5% aqueous solution of calcium hypochlorite. Alternatively, it may be glutaraldehyde, a 5.25% aqueous solution of sodium hypochlorite, a 70% aqueous solution of isopropyl alcohol, an aqueous solution of 70% ethanol alcohol, or a phenyl based solution which may include glutaraldehyde.

The closed device, due to the high concentration of fumes from the solution, is lethal to organisms, spores, bacteria, viruses and fungi.

Another embodiment is shown in FIGS. 4–8. It is easily and inexpensively manufactured, and it is quite effective for the purposes of disinfecting various types of objects.

Figure 4:
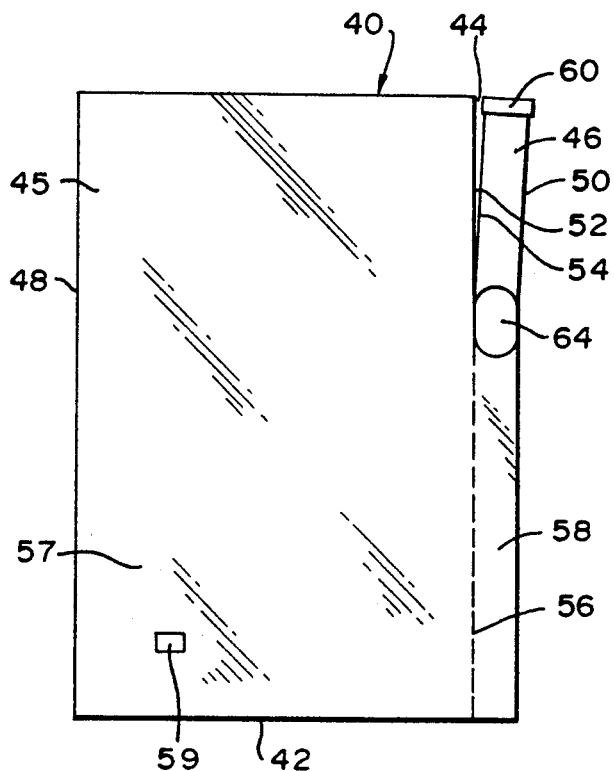
FIG. 4 is a layout view of an alternative device constructed according to the invention.

The bag 40 shown in FIG. 4 is a linerless device formed of identical front and back panels of relatively flaccid thermoplastic sheet material. The bottoms of these panels are connected together by a fold line 42. Both panels are slit at 44 to provide the bag with a main neck means 45 for introducing contaminated objects into the cavity and an auxiliary neck means 46 for introducing disinfectant solution into the device. In FIG. 4, the auxiliary neck 46 has been inclined slightly for illustrative purposes. Continuous heat seals are used to join the panels together at the side edges 48 and 50, and at the edges 52 and 54 formed by the slit. A line 56 of longitudinally oriented and longitudinally spaced heat seals extends down from the lower end of the slit 44 to define the boundary between the object-containing cavity portion 57 and a dispensing conduit portion 58. The openings in the heat seal line 56 provide outlets for releasing disinfectant solution from the conduit 58 to the cavity that contains the contaminated objects.

To alleviate the possibility of any escape of contents from the bag through the dispensing conduit before the dispensing conduit is sealed, a pad of filter material 64 is provided as shown in FIG. 4. Liquid will flow through this filter material, but the material acts much in the same manner as a surgical face mask to prevent harmful airborne particles from escaping to the atmosphere from the dispensing conduit.

Preferably, a visual sterilization indicator 59 is attached inside the cavity to provide a visible signal to confirm that sterilization is complete. Commercially available indicators of this type use spores that undergo a color change when they are killed by sterilization.

Figure 5:
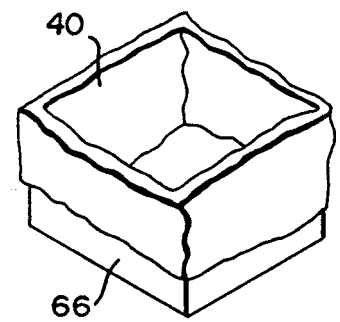
FIG. 5 is a perspective view showing the device of FIG. 4 in use.

A bag 40 constructed according to FIG. 4 is preferably used with a rigid liquid impervious receptacle 66 as shown in FIG. 5, where it can be seen that the upper portions of the bag drape over the edges of the receptacle 66, the downwardly draped portions having a sufficient length that permits gathering and tying as will be described below. The receptacle 66 is substantially rigid and waterproof so that any accidental leakage from the bag will be safely retained in the receptacle.

Figure 8:
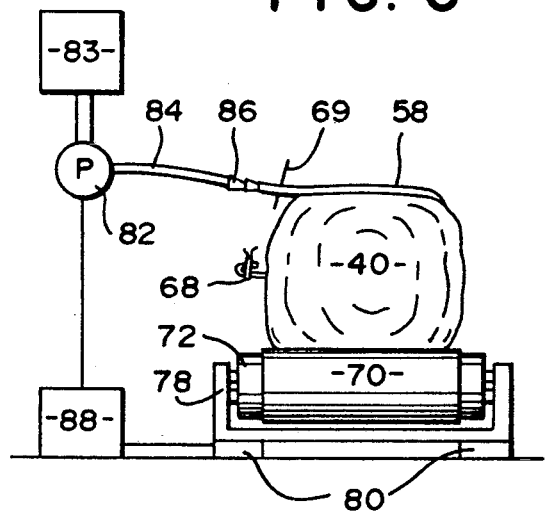

After the bag has been filled to the upper edge of the receptacle 66, the receptacle and bag 40 can be transported to a hospital "dirty room" or like location, where an attendant will lift the draped neck of the bag, gather it, twist it, fold the twisted portion into an inverted U-shape, and then apply a tie thereto as shown at 68 in FIG. 8, thus sealing the cavity of the bag.

The bag is then placed on its side as shown in FIG. 8, oriented so that the dispensing conduit is centered above the contaminated contents of the bag. A disinfectant solution such as calcium hypochlorite is poured or otherwise introduced into the dispensing conduit. This solution passes through the openings in the interrupted heat seal, and then into the bag contents.

Figure 6:
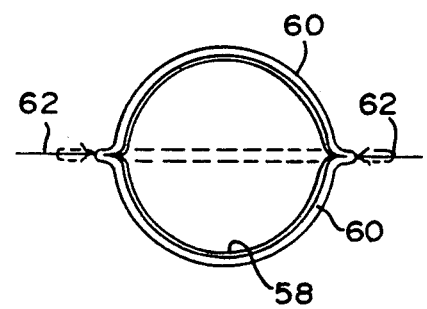
FIG. 6 is an end view of the solution-receiving neck of the device, in an open condition.

To facilitate the opening of the auxiliary neck, a pair of strips of plastic material 60 are bonded to the exterior surface of the neck as shown in FIG. 6. The pieces are normally flat so they are in the position shown in broken lines. However, they are resilient and flexible so that they and the bag material therebetween will spread apart when pressure is applied by the fingers as shown by the arrows 62 in FIG. 6. After the neck is opened in this manner, sterilization fluid is conveniently introduced into the dispensing conduit 58.

Figure 7:
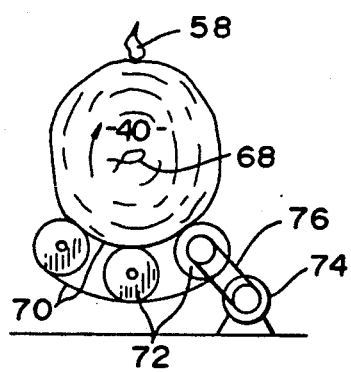
FIGS. 7 and 8 are diagrammatic end and side elevational views showing an apparatus and method for practicing the invention.

The sterilization procedure is facilitated by the apparatus schematically shown in FIGS. 7 and 8. In this apparatus, there is a bag-supporting belt 70 that rides over three rollers 72, one of which is connected to a motor 74 by a drive belt 76. The rollers are rotatably supported on a weighing platform 78 which is provided with a known type of weight-sensing device. Piezoelectric load cells 80 can be used for this purpose and two such devices are shown in FIG. 8.

A metering pump 82 delivers precisely measured quantities of disinfectant from a reservoir 83 to a hose 84 which is provided with a tapered outlet nozzle 86. This nozzle is inserted snugly into the auxiliary neck 46 of the bag so that leakage is avoided.

The metering pump is operated by a controller 88 which receives weight-indicating signals from the load cells 80 of the weighing platform and transmits quantity-determining signals to the pump 82. The pump, operating automatically, delivers a quantity of disinfectant solution which is proportional to the weight of the contents of the bag. If calcium hypochlorite solution of 5% concentration is used, 1800 milliliters of solution should be used for each pound of a bag's contents. The neck 46 of the dispensing conduit can then be sealed by twisting it, folding it, and then tying it with a tie such as the one illustrated at 69 in FIG. 8.

A few seconds after the solution has flowed from the dispensing conduit into the cavity, the motor 74 is energized so that the rollers 72 and belt 70 move to rotate the bag, preferably at least two revolutions. This rotation is at a speed selected to optimize the distribution of the solution throughout the entire cavity wall and within the contents of the cavity.

Figure 9:
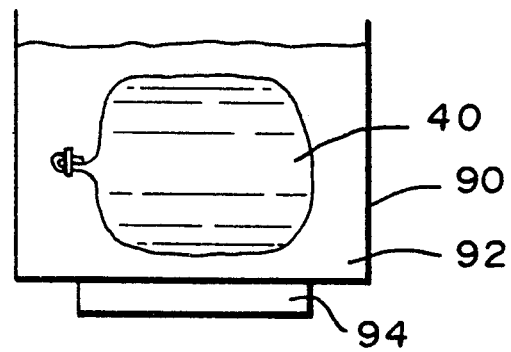
FIG. 9 illustrates a supplemental process step in which the bag, its contents and the disinfectant solution are subjected to ultrasonic energy.

In a modified procedure shown in FIG. 9, the distribution of the disinfectant solution within the bag contents is enhanced by subjecting the bag to ultrasonic energy. After the disinfectant solution has been introduced into the bag and the bag has been sealed, the entire bag 40 is immersed in a vessel 90 which contains a liquid coupling solution 92. The vessel has a transducer 94 for generating ultrasonic waves having a frequency of about 8 to 50 MHz. Cavitation waves are transmitted by the coupling solution to the bag and its contents to disperse the disinfectant solution effectively throughout the bag, to increase the temperature of the bag contents, to break up clusters of organisms so that they are more accessible to the disinfectant solution, and to provide rapid sterilization.

Figure 10:
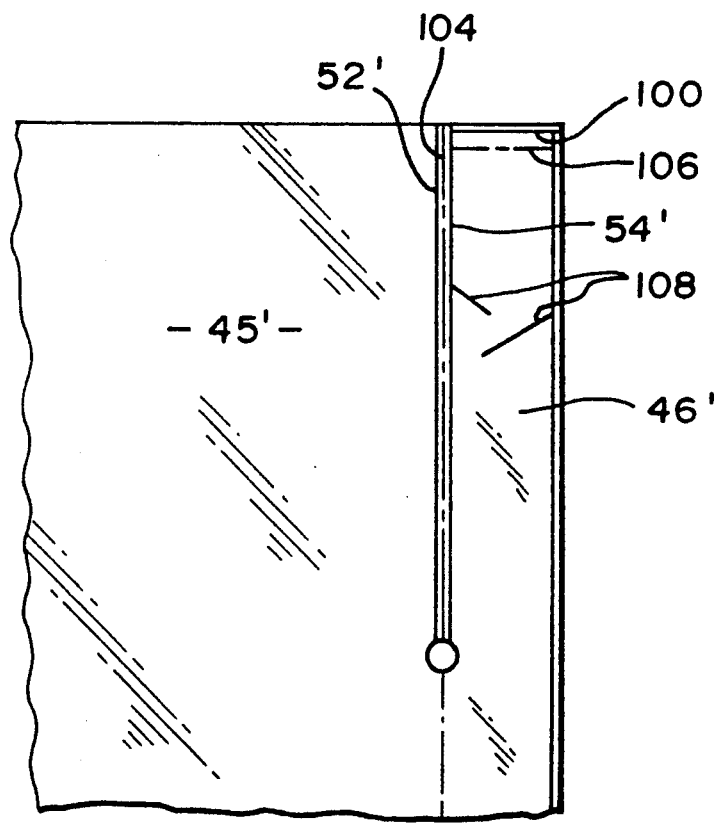
FIG. 10 shows a portion of another embodiment of a device constructed according to the invention.

FIG. 10 shows a preferred embodiment of the invention in which chain dot lines represent tearable lines of weakness. In this embodiment the inlet end of the auxiliary neck 46' is initially closed by a seal line 100, and the auxiliary neck is attached to the main neck 45' by a tear line 104. If desired, the tear line 104 can extend only a short distance from the upper edge of the device, with a slit extending downwardly therefrom. A second tear line 106 extends transversely across the auxiliary neck 46'.

Reference numerals 52' and 54' designate seal lines that run along the edges of the main neck 45' and auxiliary neck 46', respectively. Oblique seals 108 deter outward flow of liquid and vapor through the auxiliary neck in case the bag is compressed in the course of handling.

When using the bag of FIG. 10, contaminated items and other objects are placed in its cavity via the main neck 45'. Tear line 104 is then torn to separate the auxiliary neck 46' from the main neck 45'. The neck 45' is gathered, twisted, folded and tied to seal the main cavity. At this point, the undesired escape of contaminated vapors from the cavity is prevented because the end of the auxiliary neck is sealed by the seal line 100. The sealed bag can then be transported to a processing station. At the processing station, the tear line 106 is torn to remove the seal 106 and open the end of the auxiliary neck so that the disinfectant solution can be introduced as described above.

Figure 11:
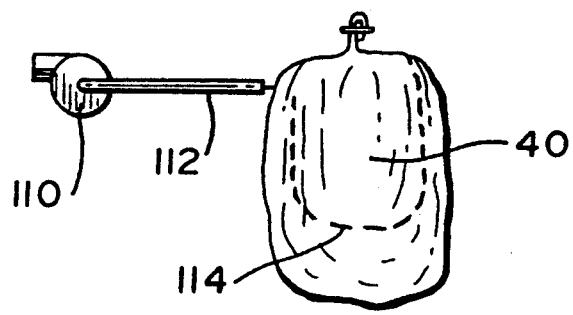
FIG. 11 shows a supplemental process step of reducing the volume of the bag cavity to promote dispersion of the disinfectant solution for effective sterilization.

Another enhancement to the process of the invention is shown in FIG. 11. This step is performed after the disinfectant solution has been introduced into the bag and the bag has been sealed. As shown in FIG. 11, a vacuum device 110 has a hose 112 provided with a needle which is inserted into the cavity of the bag 40. The vacuum device 110 is operated to create a pressure drop across the wall of the bag, thus reducing the volume of the cavity as shown by the broken line 114, and causing further distribution of the disinfectant solution throughout the contaminated contents of the bag. The needle is withdrawn and a tape or other seal is quickly placed over the opening formed by the needle to reseal the bag in its compressed condition.

The invention is useful for the sterilization of objects such as body fluids removed from a surgical site by a conventional surgical aspirator. In this case, the device is formed so the neck leading to the cavity is small enough to fit snugly over the aspirator outlet. An absorbent material such as sawdust or absorbent sheet material lining is placed in the cavity of the device. Contaminated fluids from the aspirator will flow into the cavity where it will be absorbed by the absorbent material. When the disinfectant is introduced into the cavity, it and its vapors will intimately contact the contaminated fluid to produce effective disinfection and sterilization.

Instead of twisting, folding and tying the neck of the dispensing conduit, it is possible to provide it with a fitting which has a cylindrical body, the perimeter of which is sealed to the internal wall of the dispensing conduit. A transverse wall in the fitting has a self-closing passage through which a needle can be injected or a liquid can be forced under pressure. A removable threaded plug is provided, and it preferably is retained on the device by a flexible connector as is well known in the art to prevent loss of container caps.

Although the preferred forms of the invention have been illustrated, it may take various other forms. For example, in the device of FIGS. 1–3, the disinfectant solution can be introduced at a lower area in the device so that the liquid will, by capillary action wick upwardly to impregnate the liner. Devices other than frangible ampules can be used to release the disinfectant solution into the distribution conduit, and a variety of other sealing means may be used. In view of these and other possible variations, it is emphasized that the invention is not limited only to the disclosed embodiments but embraces a wide variety of devices and methods which fall within the spirit of the following claims.

I claim:

1. A device for receiving and disinfecting biological materials, contaminated items, and other objects, comprising, a wall which forms a cavity for holding objects to be disinfected, said wall being formed of a sheet material which is substantially impervius to liquids and gases, an elongated dispensing conduit means for releasing disinfectant solution into said cavity, said dispensing conduit means having outlets which are spaced apart along its length and are positioned to release disinfectant solution into said cavity, means for introducing a disinfectant solution into the dispensing conduit means so that the disinfectant solution will be released through said outlets into spaced apart locations in said cavity, said device having an opening which permits objects to be inserted into the cavity, and sealing means for closing the opening to retain objects and disinfectant solution within the cavity so that the objects will be disinfected by the disinfectant solution and its vapors, said dispensing conduit being spaced from the sealing means.

2. A device according to claim 1 wherein the sealing means includes a drawstring which extends around the opening to constrict and close the opening, said wall being folded on itself between the drawstring and the dispensing conduit means, said drawstring also extending around the device at a location between the fold and the dispensing conduit means.

3. A device according to claim 1 wherein the means for introducing a disinfectant solution is a frangible ampule.

4. A device according to claim 1 including a disinfectant solution containing a disinfecting agent selected from the group consisting of glutaraldehyde, sodium hypochlorite, and alcohol.

5. A device according to claim 1 wherein the wall is formed of layers of polyethylene and polyester.

6. A device according to claim 1 in which an absorbent liner of sheet material is located inside the wall so as to face toward objects in the cavity, said outlets of the dispensing conduit means being positioned to release disinfectant solution into said absorbent liner.

7. A device according to claim 1 wherein the dispensing conduit means extends around the perimeter of the device.

8. A device according to claim 1 in which the dispensing conduit means extends along a side of the cavity.

9. A device according to claim 8 wherein the device is formed of two contiguous panels that are sealed together to form the cavity and the dispensing conduit means, said device having a seal formed between the conduit means and the cavity, said seal being discontinuous to provide the outlets for disinfectant solution.

10. A device according to claim 9 in which the device has a first neck and a second neck, said first neck including said opening for inserting said objects into the cavity, said second neck providing said means for introducing the disinfectant solution into the dispensing conduit means.

11. A device according to claim 10 having a tearable line of weakness which initially connects the first and second necks.

12. A device according to claim 10 having a removable seal which initially closes the second neck.

13. A device according to claim 10 having seals positioned and arranged to extend only partially across the second neck to deter outward flow of liquid and vapor through the second neck.

14. A device according to claim 1 wherein the sealing means includes a tie that encircles a gathered and folded portion of the device.

15. A device according to claim 1 wherein the cavity contains an absorbent means for absorbing contaminated liquid introduced into the cavity.

16. A method for disinfecting biological materials comprising the steps of providing a device having a wall which forms a cavity for holding objects to be disinfected, and a dispensing conduit means extending along one side of the cavity and provided with outlets which are positioned to release disinfectant solution into the cavity, said method including the steps of sealing the cavity when it contains objects that are to be disinfected, orienting the device so that the outlets extend along the upper portion of the cavity above the objects to be disinfected, introducing a disinfectant solution into the dispensing conduit so that the disinfectant solution will flow through the outlets and downward into the objects within the cavity, said disinfectant solution being provided in quantities sufficient to disinfect the objects within the cavity, and sealing the dispensing conduit means to prevent vapors from escaping the cavity via the dispensing conduit.

17. A method according to claim 16 including the step of rotating the device to distribute the disinfectant solution in the cavity.

18. A method according to claim 16 including the step of subjecting the device to ultrasonic waves after the disinfectant solution has flowed into the cavity.

19. A method according to claim 16 including the step of applying a pressure difference across said wall to reduce the volume of the cavity after the disinfectant solution has flowed into the cavity.

20. A method of disinfecting biological materials, contaminated items, and other objects, comprising the steps of:

providing a device which has a wall which forms a cavity for holding objects to be disinfected, said wall being formed of sheet material which is substantially impervious to liquids and gases, said device having an opening which permits objects to be inserted into the cavity, and an absorbent liner of sheet material which is located inside the wall so as to face toward objects in the cavity, said device having an elongated dispensing conduit which extends along said wall of the device and an outlets formed therein, and spaced apart along its length, inserting contaminated objects into said cavity, closing the opening with a sealing means, introducing a disinfectant solution into the dispensing conduit means, and releasing the disinfectant solution through said outlets into spaced apart locations in said absorbent liner until the objects are disinfected by the disinfectant solution and its vapors.

21. A method according to claim 20 including the step of subjecting the device to ultrasonic waves after the disinfectant solution has flowed into said absorbent liner.

22. A method according to claim 20 including the step of applying a pressure differential across said wall to reduce the volume of the cavity after the disinfectant solution has flowed into said absorbent liner.

* * * * *